June 20, 1939. D. AICARDI Plant Pat. 332
ROSE PLANT
Filed Dec. 10, 1938
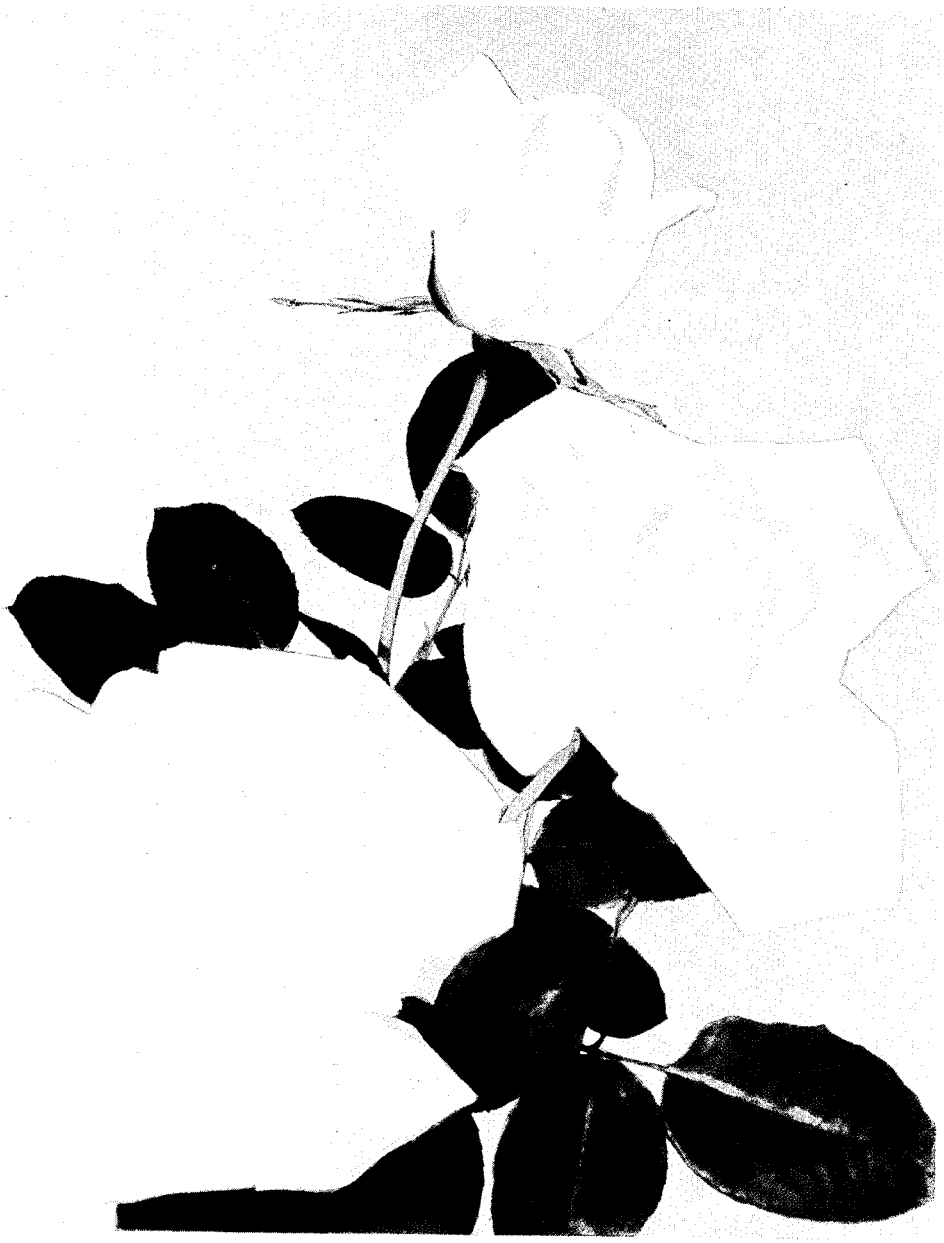
Inventor
Domenico Aicardi
By Robb & Robb
Attorneys Patented June 20, 1939

UNITED STATES PATENT OFFICE

332

ROSE PLANT

Domenico Aicardi, San Remo, Italy, assignor to Jackson & Perkins Company, Newark, N. Y.

Application December 10, 1938, Serial No. 245,041

1 Claim. (Cl. 47—61)

The present invention relates to a new and distinct, vigorous growing, bush Hybrid Tea rose. It is a seedling of Dame Edith Helen crossed with Julien Potin, particularly distinguished by the unusual color characteristics of its flower in all stages and its habits for roses of that color.

The Hermosa Pink color of the color combination is notably the clearest of all the pink colored roses while the dominating La France Pink in combination with the shape mark this variety as distinctly outstanding and novel.

One of the primary or important characteristics of the coloring is the complete absence of Violet tones in all stages of the bud and the flower.

The plant has been asexually reproduced and the characteristics noted were found to be fixed.

The following description was made from flowers grown outdoors in Newark, New York, on the morning of June 26, 1938. (All color terminology is in accordance with Ridgway's Color Chart.)

Parentage:
- *Seed parent.*—Dame Edith Helen.
- *Pollen parent.*—Julien Potin.

Classification:
- *Botanic.*—Hybrid Tea.
- *Commercial.*—Hybrid Tea.

*Flower*

Blooming habit:
- Recurrent—continuous.

Bud:
- *Size.*—Large.
- *Form.*—Long, pointed. Unaffected by wet or hot weather.
- *Color.*—When sepals first divide—Plate 1, La France Pink. When petals begin to unfurl—Plate 1, Hermosa Pink. When half blown: Inside of petals—Plate 1, Hermosa Pink. Reverse of petals—Plate 1, La France Pink.
- *Sepals.*—Serrated, "hood" above bud, curl back when bud begins to open.
- *Calyx.*—Shape—funnel. Size—small. Aspect—smooth.
- *Peduncle.*—Length—medium. Aspect—prickly. Color—Plate 31, Rainette Green. Strength—stiff.
- *Opening.*—Bud opens well, and is unaffected by adverse conditions.

Bloom:
- *Size.*—Large. Average size when fully expanded—4½ inches.
- *Borne.*—Singly.
- *Stems.*—Medium, normal.
- *Form.*—When first open, high center.
- *Permanence.*—Retains its form to the end, flattens.
- *Petalage.*—Double (full but open center). Number of petals under normal conditions—25.
- *Color.*—Center of flower—Plate 1, Hermosa Pink. Outer petals—Plate 1, La France Pink. Base of petals (aiglet)—Plate 4, Lemon Chrome. Inside of petals—Plate 12, Rose Pink. Reverse of petals—Plate 1, La France Pink.
- *Discoloration.*—General tonality at end of first day—Plate 1, La France Pink. Second and third days—Plate 12, Rose Pink.

Petals:
- *Texture*—Thin. Is unaffected by wet or hot weather.
- *Appearance*—Inside—satiny. Outside—satiny.
- *Form.*—Oval, pointed.
- *Arrangement.*—Informal (with "rags" in center). Petaloids in center—few, small.
- *Persistence.*—Drop off cleanly.
- *Fragrance.*—Strong. Nature—"Old Rose" perfume (Centifolia).
- *Lasting quality on the plant.*—Long. As cut flowers—long.

Genital organs:
- *Stamens, anthers.*—Large, many. Color—Plate 4, Light Cadmium. Arrangement—regular round styles.
- *Stamens, filaments (threads).*—Medium. Color—Plate 4, Apricot Yellow.
- *Pollen.*—Plate 4, Light Cadmium.
- *Styles.*—Bunched, uneven length, medium, heavy.
- *Stigmas.*—Color—Plate 4, Empire Yellow.
- *Ovaries.*—Some protruding from calyx.

Fruit:
- Variety is fertile with its own pollen.
- *Form.*—Round.
- *Aspect.*—Smooth.
- *Sepals.*—Permanent, curled.

*Plant*

Form:
- Bush.

Growth:
- Vigorous, upright, branching.

Foliage:
- Five-seven leaflets.
- *Size.*—Medium.
- *Quantity.*—Abundant.

*Color.*—New foliage: Upper side—center—Plate 31, Dark Cress Green. Edge—Plate 26, Dahlia Carmine. Under side—Plate 26, Dahlia Carmine. Old foliage: Upper side—Plate 31, Dark Cress Green. Under side—Plate 31, Light Cress Green.

*Shape.*—Oval pointed.

*Texture.*—Upper side—smooth, flat. Under side—smooth. Ribs and veins—ordinary.

*Edge.*—Serrated (saw toothed).

*Serration.*—Single, small.

*Rachis.*—Color—Plate 31, Light Cress Green. Under side—rough, prickles.

*Stipules.*—Short, bearded.

*Disease resistance.*—Resistant.

Wood:

*New wood.*—Color—Plate 26, Dahlia Carmine. Bark—rough.

*Old wood.*—Color—Plate 31, Jade Green. Bark—rough.

Thorns (Divided into thorns, prickles and short needles):

*Thorns.*—Quantity—On main stalks from base—ordinary. On laterals from stalk—ordinary. Form—narrow base, medium length, straight. Color when young—Plate 13, Pompeian Red. Position—irregular.

*Prickles.*—Quantity—On main stalks—many. On laterals—many. Color—Plate 13, Pompeian Red.

*Short needles.*—Quantity—On main stalks—few. On laterals—few.

I claim:

A new and distinct variety of Hybrid Tea rose plant characterized as to novelty by the pink coloring of its flower and the habits of the plant for roses of that color, and the absence of violet tones in all stages of the bud and the flow, substantially as shown and described.

DOMENICO AICARDI.